(12) United States Patent
Singer

(10) Patent No.: US 12,296,131 B1
(45) Date of Patent: May 13, 2025

(54) TRANSDERMAL DRUG DELIVERY WITH A FORCE-CALIBRATED MAGNETIC MICRONEEDLE PATCH

(71) Applicant: Leili E. Singer, Chestnut Hill, MA (US)

(72) Inventor: Leili E. Singer, Chestnut Hill, MA (US)

( * ) Notice: Subject to any disclaimer, the term of this patent is extended or adjusted under 35 U.S.C. 154(b) by 0 days.

(21) Appl. No.: 19/017,212

(22) Filed: Jan. 10, 2025

(51) Int. Cl.
A61M 37/00 (2006.01)

(52) U.S. Cl.
CPC . *A61M 37/0015* (2013.01); *A61M 2037/0023* (2013.01); *A61M 2205/0288* (2013.01); *A61M 2210/0662* (2013.01)

(58) Field of Classification Search
CPC ...... A61M 37/0015; A61M 2037/0023; A61M 2205/0288; A61M 2210/0662
USPC ......................................................... 604/173
See application file for complete search history.

(56) References Cited

U.S. PATENT DOCUMENTS

| | | |
|---|---|---|
| 2008/0200883 A1 | 8/2008 | Tomono |
| 2009/0118662 A1 | 5/2009 | Schnall |
| 2009/0235688 A1* | 9/2009 | Oh .................... A61H 39/04 63/12 |
| 2010/0208049 A1 | 8/2010 | Yu et al. |
| 2011/0201869 A1 | 8/2011 | Edwards et al. |
| 2017/0087364 A1 | 3/2017 | Cartledge et al. |
| 2020/0164193 A1* | 5/2020 | Williams ............. A01K 11/001 |
| 2022/0047859 A1 | 2/2022 | Nejad et al. |

FOREIGN PATENT DOCUMENTS

| | | | |
|---|---|---|---|
| WO | WO-2012006677 A1 * | 1/2012 | ........... A61B 17/205 |
| WO | WO 2022/241170 A1 | 11/2022 | |

OTHER PUBLICATIONS

Smith et al., "The clinical and translational prospects of microneedle devices, with a focus on insulin therapy for diabetes mellitus as a case study," International Journal of Pharmaceutics, Nov. 25, 2022, 628:122234.

* cited by examiner

*Primary Examiner* — Phillip A Gray
(74) *Attorney, Agent, or Firm* — Fish & Richardson P.C.

(57) ABSTRACT

Provided herein are devices and methods for transdermal delivery of drugs into the systemic circulation, including a drug-loaded microneedle patch and a force-calibrated tractive counterpart. The tractive counterpart provides a force that is calibrated to hold the microneedles in the skin but not to impair capillary perfusion. Embodiments are described that comprise two microneedle patches, e.g., wherein the microneedles of one such patch are staggered with reference to the other patch, and wherein the weight of the patches is controlled to allow the device to remain in place despite movement of the subject who wears it.

9 Claims, 9 Drawing Sheets

FIG. 3A
FIG. 3B
FIG. 3C
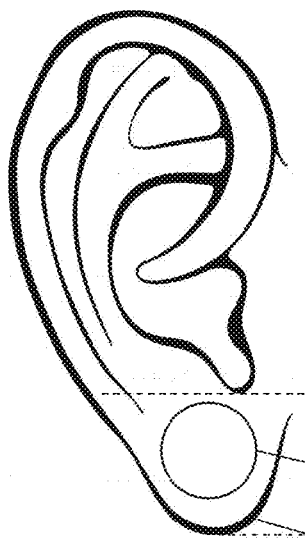
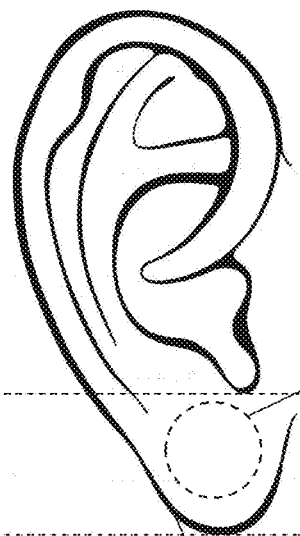
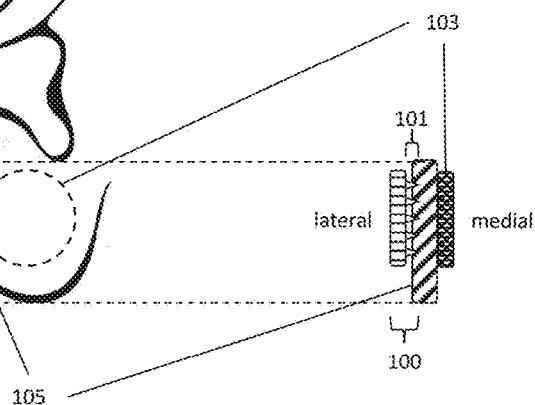

TRANSDERMAL DRUG DELIVERY WITH A FORCE-CALIBRATED MAGNETIC MICRONEEDLE PATCH

FIELD OF THE INVENTION

This disclosure relates to devices and methods for transdermal drug delivery. More specifically, the disclosure relates to devices and methods for delivering a drug across the skin, comprising at least one drug-loaded microneedle patch and at least one force-calibrated, magnetic, tractive counterpart.

BACKGROUND

Most drugs are taken by the oral route, but some drugs cannot be delivered in this way. In such cases, a drug for systemic use is typically delivered by hypodermic needle (e.g., subcutaneously or intramuscularly). Such needles, however, cause pain, provoke anxiety, and require special means of waste disposal. There has been much interest in devices and methods to circumvent the need for hypodermic needles. Microneedles are substantially smaller than hypodermic needles yet can penetrate the stratum corneum, which is the principal barrier to drug diffusion across the skin. Many types of drug-loaded microneedles have been described. See, e.g., Smith et al., The clinical and translational prospects of microneedle devices, with a focus on insulin therapy for diabetes mellitus as a case study, *Int. J. Pharmaceutics* 2022; 628:122234. Most types of drug-loaded microneedles are pressed into the skin for a period of several hours, during which the drug diffuses into skin capillaries and into the systemic circulation.

This raises a technical problem: the need to hold microneedles at a proper depth and position in the skin for several hours. Until now, a typical solution to this problem has been to mount an array of microneedles on a solid or semi-flexible adhesive backing to form an adhesive patch. See, e.g., Smith, et al., supra. Typically, the adhesive surrounds the microneedles. When the adhesive patch is applied to the skin, the backing exerts a tangential, spring-like force on the microneedles that tends to push the microneedles into the skin. However, this force is inconsistent, as most of it is tangential to the skin; the vector component that is normal to the skin is not uniform across all microneedles in the array; the adhesive and backing loosen over time; and the microneedles or patch slide due to patient movement.

There is, therefore, a need for new devices to keep microneedles in a stable position in the skin for a sufficient period of time, e.g., several hours.

SUMMARY

The present disclosure arises out of the inventor's efforts to develop microneedle patches with a magnetic tractive counterpart to hold the microneedles in place. This effort can be understood by reference to the embodiment of FIG. 1, where a microneedle patch 100 includes a plurality of drug-loaded microneedles 101 on a ferromagnetic backing 102; and a tractive counterpart 103 comprises a permanent magnet 104. Thus constructed, the patch 100 and tractive counterpart 103 can be placed, for example, on opposite sides of a suitable site on a subject, e.g., the lobule or antihelix of a human ear.

However, the inventor encountered an unexpected problem with this approach: the attractive force between the ferromagnetic and magnetic parts compressed the skin and reduced perfusion, i.e., reduced blood circulation. This phenomenon was observed by blanching of the skin and was confirmed by the loss of signal on transmissive pulse oximetry.

This reduced perfusion, which is a restriction in capillary blood flow, interferes with the operation of the drug-loaded microneedles, which depend on that capillary blood flow to transfer the drug into the systemic circulation. A device that reduces perfusion is undesirable.

Therefore, the inventor devised microneedle patches with tractive counterparts that would (1) maintain a substantially constant attractive force between them; wherein the attractive force was (2) at least sufficient to hold the microneedles in place in the skin; but (3) did not reduce capillary blood flow. In some embodiments, this is further helped by (4) the exploitation of shear forces provided by microneedles oriented perpendicular to gravitational force.

Thus, in a first aspect, the disclosure provides devices that include: a microneedle patch including a plurality of drug-loaded microneedles mounted on a backing comprising a ferromagnetic material; and a tractive counterpart comprising a permanent magnet; wherein, when the patch and backing are placed on a suitable site on the human body (e.g., they are parallel to, and about 3.2 mm apart from, one another) the pressure applied to the skin by either the patch or the backing, or both, is less than 0.8 Newtons per square centimeter ($N/cm^2$). In practice, for many applications on humans, the patch and backing can be, e.g., about 2 mm to about 6 mm apart. In some embodiments, a minimum separation, e.g., 3.2 mm, can be specified, such that the pressure applied to the skin with that separation is less than 0.8 $N/cm^2$. The pressure must, however, be sufficient to hold the microneedles in place, e.g., at least 0.1 $N/cm^2$. Thus, in some embodiments, the pressure applied to the skin is between 0.1 and 0.8 $N/cm^2$.

As explained further herein, the pressure can be controlled, e.g., by controlling the magnetic field strength of the magnet, the distance between the magnet and the backing, and/or the area of the microneedle patch or the backing that is in contact with the skin.

In some embodiments, the aforementioned backing includes a permanent magnet. Thus, such embodiments include two permanent magnets that are attracted to one another.

In another aspect, the disclosure provides devices including two microneedle patches, each having a planar array of drug-loaded microneedles mounted on a backing. At least one of the backings includes a permanent magnet, and the other backing includes a permanent magnet or a ferromagnetic material. Likewise, in this embodiment, the pressure applied to the skin by either of the backings, or both, is between 0.1 and 0.8 $N/cm^2$. Embodiments including two microneedle patches that are attracted to one another have a beneficial property insofar as they can deliver drug about twice as efficiently compared to embodiments comprising only one microneedle patch of the same type. Furthermore, in embodiments having two microneedle patches, the microneedles can be advantageously staggered, as described herein.

In addition to providing superior drug delivery, the present microneedle devices provide several other advantages. For example, the microneedles exploit shear force to hold the device in place (e.g., against gravity or subject acceleration). In some embodiments, e.g., when the device is placed on the lobule of the ear, the axes of the respective microneedles are substantially horizontal (i.e., substantially perpendicular to the gravitational force); as described below, this orientation provides the benefits of shear forces. The disclosure provides devices and methods to avoid the use of adhesives, which, aside from their poor performance and tendency to detach in unwanted fashion, are sticky, irritating, difficult to remove or reposition, and prone to leave undesired residue on the skin.

The microneedle devices can be ornamented. For example, in some embodiments where the device is placed on the lobule of the ear, and it can be ornamented to have the appearance of an earring, thus concealing the nature of the device as a drug delivery patch.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and from the claims

BRIEF DESCRIPTION OF THE DRAWINGS

FIG. 3A is a lateral view of the external ear and a microneedle patch as described herein.

FIG. 3B is a lateral view of the external ear and a magnetic tractive counterpart.

FIG. 3C is a cross-sectional view of a microneedle patch and magnetic tractive counterpart with respect to the lobule of a human ear.

DETAILED DESCRIPTION

Definitions

Figure 1:
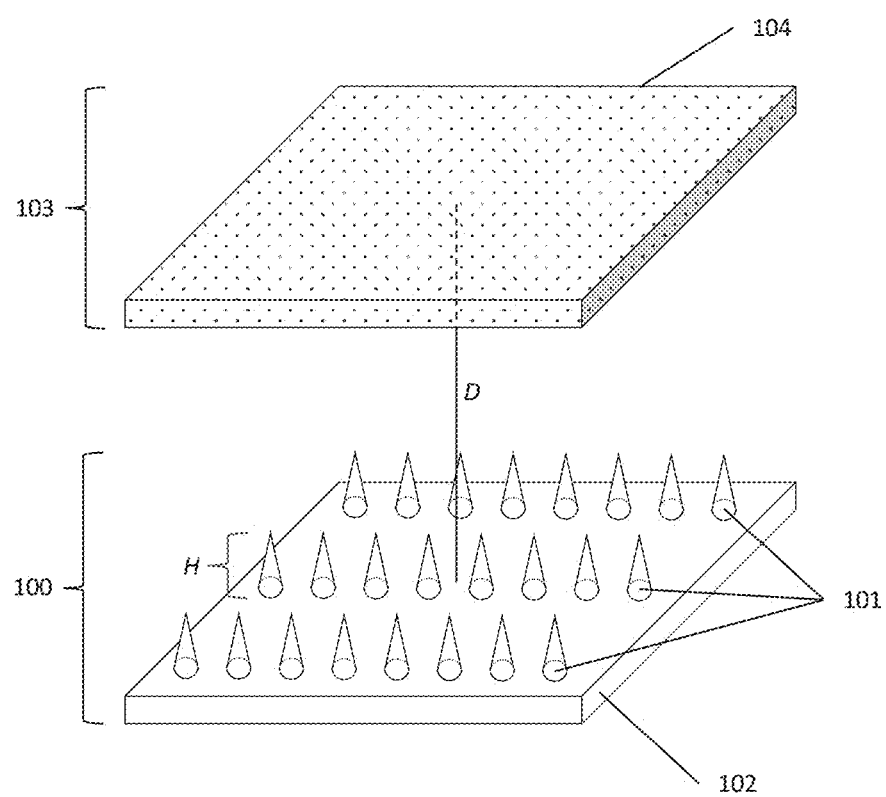
FIG. 1 is a perspective view of an embodiment of a device including a microneedle patch and a tractive counterpart comprising a permanent magnet, as disclosed herein.

As used herein, the "axial projection" of a microneedle means the locus of all lines that satisfy two conditions: (1) perpendicular to a backing and (2) intersect the microneedle. In embodiments wherein the backing is not strictly planar, a hypothetical, e.g., best-fit, plane can be defined for purposes of determining what lines are perpendicular to the plane.

As used herein, the "axis" of a microneedle is a line defined by two points, which points are the apex of the microneedle and the center of the base of the microneedle; or, if that base is not a symmetric form, then the centroid of the base of the microneedle. For purposes of this definition, "base" refers to a cross-sectional geometric form where the microneedle contacts its backing.

As used herein, "backing" means a rigid or semi-rigid, substantially planar part or material that attaches to and supports the base of a microneedle and optionally connects a plurality of microneedles.

As used herein, "face area" refers to the cross-sectional area of the backing in the plane where the backing meets the base of the microneedles.

As used herein, "horizontal" means horizontal with respect to the earth.

As used herein, "microneedle" means a sharp rigid or semi-rigid pointed structure, 25 to 2000 microns in length, comprising a sharp apex and a base that is broader than the apex, wherein the apex can penetrate into skin or an epithelium (e.g., a mucous membrane) of a subject. A "drug-loaded" microneedle is a microneedle comprising a drug which is adapted to release the drug when in contact with a subject, e.g., a human.

As used herein with reference to a first plurality of microneedles on a substantially planar first backing and a second plurality of microneedles on a substantially planar second backing, the term "staggered" means that the first backing, the second backing, the first plurality of microneedles, and/or the second plurality of microneedles are arranged such that no axial projection of any of the first plurality of microneedles overlaps with any axial projection of the second plurality of microneedles.

As used herein, "normal to the skin" and similar phrases refer to a direction that is perpendicular or substantially perpendicular to a plane defined by the surface of the skin. Where the skin is not exactly planar or is wrinkled, "normal" to the skin means approximately normal to the skin, to the extent practicable.

As used herein, unless otherwise clear from the context, "subject" or "patient" refers to a human or animal to whom a microneedle patch is applied, or to which a drug is administered.

As used herein with reference to two backings, "substantially parallel" means that the planes that best describe the backings are parallel or deviate no more than 15 degrees in orientation from one another in any dimension (excluding rotation in the dimensions of such planes).

As used herein, the axis of a microneedle is "substantially perpendicular" to a plane of reference if the angle between that axis and the plane of reference is between 75 degrees and 105 degrees, inclusive.

As used herein, "substantially planar" includes a structure or material that is planar or substantially planar on at least one face. As used herein, a backing is substantially planar if all points on at least one face of the backing are within 0.25T of one another in the dimension that is perpendicular to the best-fit plane of those points, where T is the shortest dimension of the face in that best-fit plane.

As used herein, "systemic drug delivery" means administering a drug to a subject so that the drug reaches a concentration in the bloodstream, e.g., the plasma or serum.

Operating Principle of the Microneedle Patch Devices

In one aspect, the present disclosure provides drug-loaded microneedle patches that are intended for application to the skin of a subject and secured in place by a magnetic tractive force that is normal to the skin. The tractive force is provided by a tractive, e.g., magnetic, counterpart. In some cases, the tractive force is applied or generated by a pressure controlled, spring loaded clip rather than magnets. The clip can be a single-piece hinge design.

Crucially, the tractive force is calibrated so that the pressure of the device on the skin is below a threshold that would reduce capillary perfusion at the site where the device is applied. Such reduction of capillary perfusion would be undesirable because drug-loaded microneedle patches rely on local capillary blood flow for the drug to diffuse into the systemic circulation.

Reduction or impairment of capillary perfusion can be observed on physical exam by blanching of the skin; can be measured objectively, e.g., by transmissive pulse oximetry; and can be quantified, e.g., by Doppler ultrasonography.

The inventor has determined that for purposes of the present disclosure, the pressure exerted against the skin by the inventive device or any of its parts (e.g., the microneedle patch or the tractive counterpart) should not exceed 0.8 Newtons per square centimeter ($N/cm^2$). See, e.g., Example 1. With this limitation on pressure, a skilled person might raise concern that the device—which necessarily comprises dense materials—is prone to detach from the subject due to sudden acceleration of the subject, e.g., when a patient wearing the device plays a sport. However, the inventor has fortuitously discovered that the microneedles, when inserted in the skin, exert shear forces sufficient to resist such inertial detachment. This, combined with control of the device's weight, provides a working solution.

Structure of the Microneedle Patch Devices

An example of a structure of a microneedle device can be understood by reference to FIG. 1. The device of FIG. 1 comprises: a microneedle patch 100 comprising a plurality of drug-loaded microneedles 101 of height H, the bases of which are mounted on a rigid or semi-rigid backing 102, wherein the backing comprises a ferromagnetic material; and a tractive counterpart 103 comprising a permanent magnet 104; wherein the shape, dimensions, and compositions of the backing 102, its ferromagnetic material, and permanent magnet 104 are selected such that, when applied to the skin, backing and the tractive counterpart, or combination thereof, exert a pressure on the skin of no more than 0.8 Newtons per square centimeter. With respect to the device, this can be expressed as: (1) the attractive magnetic force between the microneedle patch 100 and the tractive counterpart 103 when placed in a substantially parallel position at a distance D (as shown in FIG. 1 (e.g., of 3 mm to 5 mm) divided by (2) the total face area (defined herein) of the microneedle patch and the tractive counterparts.

Figure 2:
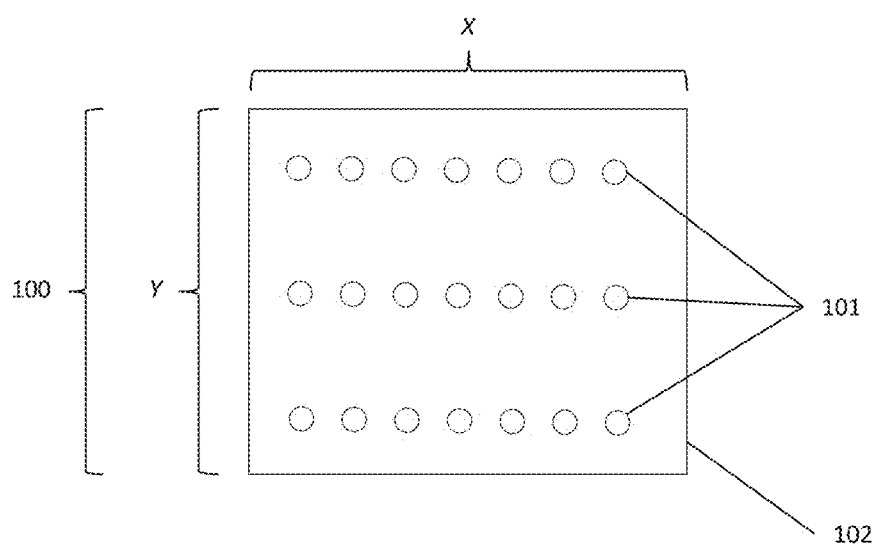
FIG. 2 is a top view of the microneedle patch component of FIG. 1.

The total face area of the inventive device can be understood by reference to FIG. 2, where the microneedle patch 100 is shown from above (i.e., perpendicular to the plane of patch). Microneedles 101 can be seen over the backing 102, which comprises a ferromagnetic material. Where X and Y refer to the dimensions of the backing, the face area is the product XY.

The placement of the inventive device with respect to the skin can be understood by reference to FIG. 3. FIG. 3A shows the external ear of a human, where a microneedle patch 100 is applied to the lateral surface of the lobule 105. In FIG. 3B, the tractive counterpart 103 is placed on the opposite (i.e., medial) side of the lobule 105; the tractive counterpart 103 is shown in a dotted line to indicate that it is hidden from view behind the lobule. The side view of FIG. 3C further illustrates the spatial relationship of the microneedle patch 100, lobule 105, and tractive counterpart 103. Note that that the microneedle patch 100 and tractive counterpart 103 are on opposite sides (lateral and medial, respectively) of the lobule 105 but aligned with one another in the other two dimensions, and the microneedles 101 are directed into the skin of the lobule 105 so that they can release drug into the skin of lobule 105.

Note that in FIG. 3C the axes of microneedles 101 are normal to the skin and, with the external ear thus oriented (i.e., with the subject's head level, in the upright position), the microneedles 101 are horizontal. The microneedles 101 are thus embedded in skin perpendicular to gravitational forces, which provides shear forces to counteract effects of gravitational acceleration on microneedle patch 100. Thus, in some embodiments, the microneedle patch and tractive counterpart are constructed for placement such that the axes of microneedles 101 will be horizontal when the head of the subject is in the upright position.

Optionally, the surface of microneedle patch 100 that is opposite from the microneedles 101 (the "free surface") can serve as the attachment site for ornamentation, e.g., in the manner of jewelry, e.g., in the manner of an earring. The free surface can, for example, be attached to or bonded with: a film, foil, paint, enamel, metal, stone, or other decorative material. In some embodiments, the free surface is attached to a layer of enamel. In some embodiments, the free surface is attached to a layer of paint. In some embodiments, the free surface is attached to a gemstone. In some embodiments, the free surface is attached to a layer comprising an alloy comprising gold, silver, platinum, or titanium.

In some embodiments, with reference to FIGS. 1 and 3, the backing 102 of the microneedle patch 100 comprises a permanent magnet, such that the inventive device comprises two permanent magnets (the other permanent magnet being the permanent magnet 104 of tractive counterpart 103). For placement on a subject (e.g., the skin of the lobule 105) the two permanent magnets (i.e., the first permanent magnet of backing 102 and the second permanent magnet 104) are oriented such that the magnets are attracted to one another. In some embodiments, the magnets are each substantially planar in shape and, when placed on a subject, are substantially parallel to one another.

Figure 4:
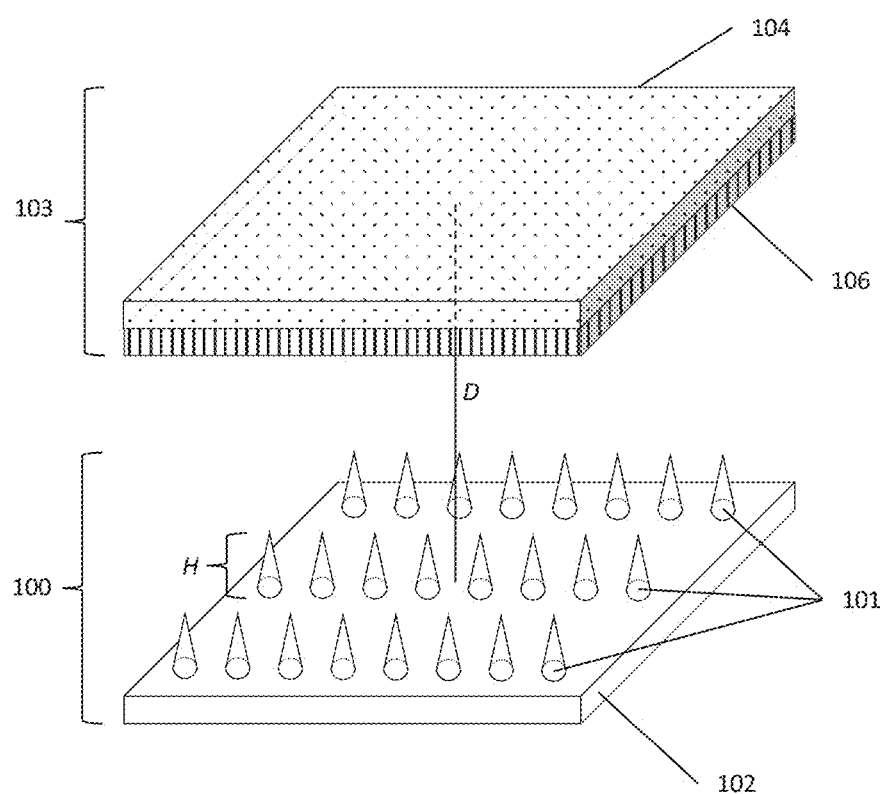
FIG. 4 is a perspective view of an embodiment of a device including a microneedle patch and a two-layered tractive counterpart as described herein.

In some embodiments, with reference to FIG. 4, the tractive counterpart 103 comprises a permanent magnet 104 and a ferromagnetic layer 106, wherein the ferromagnetic layer 106 is magnetized by the permanent magnet 104.

Figure 5:
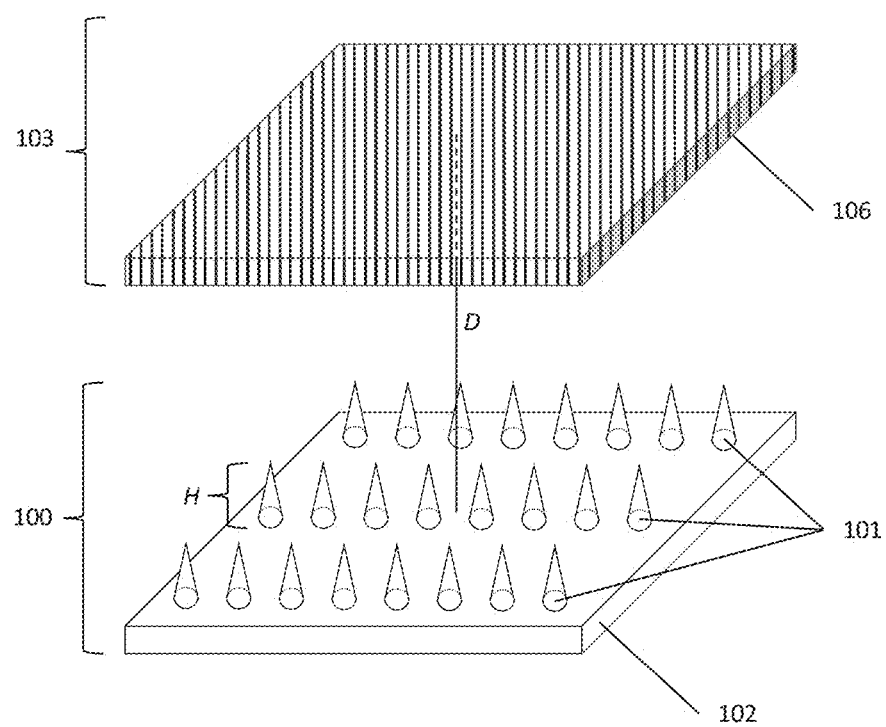
FIG. 5 is a perspective view of an embodiment of a device including a microneedle patch having a permanent magnet, and a tractive counterpart, as described herein.

In some embodiments, with reference to FIG. 5, the microneedle patch 100 comprises a backing 102 that is a permanent magnet, and the tractive counterpart 103 comprises a ferromagnetic layer 106 which is not a permanent magnet, wherein the tractive counterpart 103 does not comprise a permanent magnet.

The skilled person will thus appreciate from FIGS. 1, 3, 4 and 5 that some embodiments for the inventive device can include any one of (a), (b) or (c) as follows:
  a. a microneedle patch comprising a permanent magnet and a tractive counterpart comprising a ferromagnetic layer, wherein the layer is not a permanent magnet;
  b. a microneedle patch comprising a permanent magnet and a tractive counterpart comprising a permanent magnet; or
  c. a microneedle patch comprising a ferromagnetic material, wherein the microneedle patch does not comprise a permanent magnet, and a tractive counterpart comprising a permanent magnet.

In embodiments wherein the microneedle patch comprises a permanent magnet and the tractive counterpart comprises a permanent magnet, the two magnets should be oriented so that they are attracted to one another.

Drug-Loaded Microneedles

The production and selection of drug-loaded microneedles is known in the art. See, e.g., Smith et al., The clinical and translational prospects of microneedle devices, with a focus on insulin therapy for diabetes mellitus as a case study, *Int. J. Pharmaceutics* 2022; 628:122234; and U.S. Patent Publication 2022/0047859 A1 of Nejad et al; each of which is incorporated herein by reference. For purposes of this disclosure, a drug-loaded microneedle includes any sharp structure having a height of about 0.5 mm to about 2 mm that comprises a drug and is intended to deliver the drug across an epidermal or epithelial barrier. Microneedles can contain, without limitation, a low-molecular weight (LMW) molecule; a chemical small molecule, a macromolecule, e.g., a polypeptide, protein (e.g., monoclonal antibody), or a nucleic acid (e.g., DNA or mRNA); or a nanoparticle or exosome. The drug can be, e.g., in solution, suspension, or semisolid or solid form.

In various embodiments, the microneedles of a microneedle patch can be of uniform height or can vary in height. Likewise, the microneedles of a microneedle patch be of uniform shape or can vary in shape. The microneedles can be placed in an array that is uniformly spaced or arranged in any other suitable way. In some embodiments, it is preferable to place the microneedles in an array that is not uniformly spaced. The microneedles can be arranged at any suitable spatial density. Generally, the height, arrangement, and spacing of the microneedles will be adjusted to achieve the desired degree of penetration into the skin and the desired degree of drug delivery.

In some embodiments, the microneedles of a microneedle patch are loaded with a total drug mass is between about 1 microgram and about 1 gram. In some embodiments, the total drug mass is between about 10 micrograms and about 100 milligrams. In some embodiments, the total drug mass is between about 100 micrograms and about 10 milligrams. In some embodiments, the total drug mass is between about 300 micrograms and about 3 milligrams. In some embodiments, the total drug mass is between about 1 milligram and about 5 milligrams. In some embodiments, the total drug mass is between about 300 micrograms and about 1.5 milligrams.

In some embodiments, the microneedles of a microneedle patch deliver into the skin of a subject a total drug mass between about 1 microgram and about 1 gram. In some embodiments, the total drug mass delivered is between about 10 micrograms and about 100 milligrams. In some embodiments, the total drug mass delivered is between about 100 micrograms and about 10 milligrams. In some embodiments, the total drug mass delivered is between about 300 micrograms and about 3 milligrams. In some embodiments, the total drug mass delivered is between about 1 milligram and about 5 milligrams. In some embodiments, the total drug mass delivered is between about 300 micrograms and about 1.5 milligrams. For purposes of this disclosure, the mass of drug delivered into the skin of a subject can be measured, for example, by applying a microneedle patch containing [x] mass of drug for a desired period of time, removing the patch, swabbing the skin surface where the patch had been placed to remove any unabsorbed drug, measuring the mass of unreleased drug [y] remaining in the microneedle patch, measuring the mass of unabsorbed drug [z] swabbed from the skin surface, and calculating the difference that is [x]−[y]−[z].

Magnets and Ferromagnetic Materials

The production and selection of permanent magnets is known in the art. In some embodiments, rare earth magnets, e.g., neodymium magnets, are preferred because of the magnetic field strength they provide in relation to their mass. The production and selection of ferromagnetic materials is known in the art. Generally, a permanent magnet is a ferromagnetic material. In some embodiments, oxidation-resistant ferromagnetic materials are preferred. In some embodiments, a part comprising a ferromagnetic material can be coated, e.g., with a biocompatible plastic, e.g., to prevent oxidation and/or improve biocompatibility. In some embodiments, a backing comprises a permanent magnetic material and a second ferromagnetic material. Non-magnetic ferromagnetic materials are known in the art and can also be coated, e.g., with a biocompatible plastic.

Control of Tractive Force

For the present disclosure, the attractive (tractive) force between a magnet and its ferromagnetic counterpart is controlled to provide the microneedle patch devices with necessary purchase on the skin of a subject without interfering with perfusion at the site of placement. The tractive force between a permanent magnet and a non-magnetic, ferromagnetic counterpart as a function of distance between the parts can be determined empirically, e.g., as the pull force. Such methods are known in the art. Likewise, the tractive force between two permanent magnets as a function of distance between the magnets can be determined empirically, e.g., as the pull force. The force F between two magnetic dipoles is approximately:

$$F = \frac{\mu q_{m1} q_{m2}}{4\pi r^2}$$

Where $\mu$ is the permeability of the intervening medium, $q_{m1}$ and $q_{m2}$ are the magnitudes of magnetic charge on the magnetic polies, and r is the separation. Some embodiments of the disclosure use cylindrical magnets. In certain embodiments comprising a first cylindrical magnet and an identical second cylindrical magnet as counterpart, the force F(x) between the two cylindrical magnets is approximately:

$$F(x) = \frac{3\pi\mu_0}{2} M^2 R^4 L^2 \frac{1}{x^4} = \frac{3\mu_0}{2\pi} M^2 V^2 \frac{1}{x^4} = \frac{3\mu_0}{2\pi} m_1 m_2 \frac{1}{x^4}$$

Where $\mu_0$ is the permeability of the intervening medium; m is magnetic dipole defined as MV, where M is the magnetization field and V is the magnet volume; R and L are, respectively, the radius and length of each magnet; and x is the separation.

Thus, in some embodiments, for purposes of operation of the disclosure, the attractive force between a magnet and its ferromagnetic counterpart can be controlled by: selection of magnet(s) (i.e., with respect to composition, dipole, dimensions and/or shape); where applicable to a non-magnetic ferromagnetic counterpart, by selection of composition, dimensions and/or shape; and by selection of the distance (i.e., separation) between a magnet and its ferromagnetic counterpart.

Because separation influences the tractive force, for purposes of description herein, a minimum separation can be specified so as to avoid excessive skin compression that would adversely affect perfusion, e.g., 3.2 mm, whereby at or above this separation, the pressure on the skin must be no more than 0.8 Newtons per square centimeter.

Figure 6:
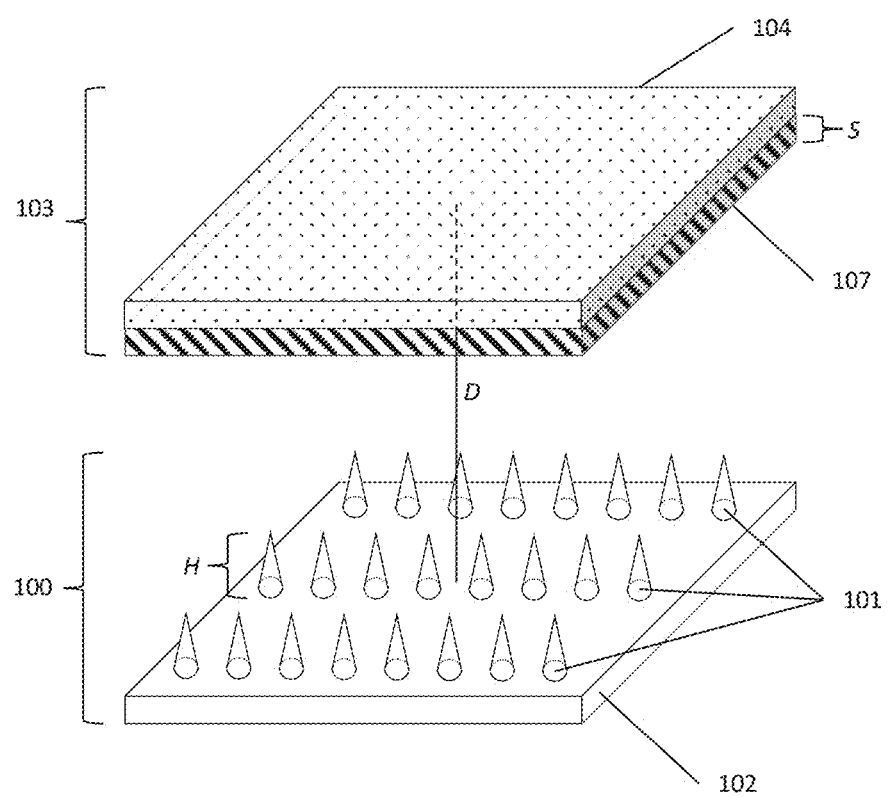
FIG. 6 is a perspective view of an embodiment of a device including a microneedle patch, and a tractive counterpart having a permanent magnet and a non-magnetic, non-ferromagnetic spacer, as disclosed herein.

A minimum separation can be obtained, for example, with reference to FIG. 6, by placing a spacer 107 of non-magnetic, non-ferromagnetic material on tractive counterpart 103 such that when a microneedle patch device is placed on the application site of a subject, the spacer contacts the skin of subject and causes the separation to be higher than it would be without the spacer. The spacer can be constructed of any suitable material. In some embodiments, the spacer is constructed of a lightweight, sturdy, waterproof biocompatible material such as a plastic. The spacer in FIG. 6 is shown as a solid layer, but in other embodiments, the spacer is discontinuous. For example, the spacer can consist of a perforated layer, a lattice, or an array of posts; a benefit of such discontinuous spacers is to allow circulation of air. In some embodiments, one or more microneedles of the device act as the spacer. In some embodiments, the length or shape of the microneedles is selected to obtain a desired degree of separation.

FIG. 6 shows the use of a spacer 107 attached to a permanent magnet 104. With reference to FIG. 5, a spacer can be similarly attached to the ferromagnetic layer 106 which is not a permanent magnet (not shown).

Figure 7:
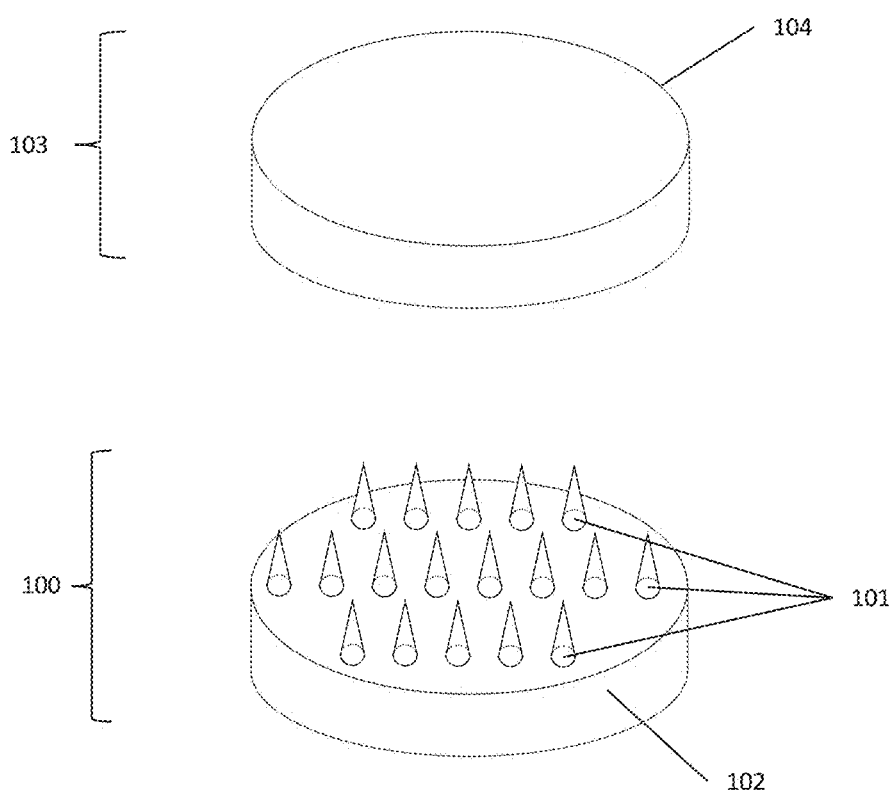
FIG. 7 is a perspective view of an embodiment of a device including a cylindrical microneedle patch and a cylindrical tractive counterpart, as described herein.

An inventive device can use parts that are circular in cross-section or cylindrical in shape. FIG. 7 shows an inventive device comprising a microneedle patch 100 comprising a plurality of drug-loaded microneedles 101, the bases of which are mounted on a rigid or semi-rigid, cylindrical backing 102, wherein the backing comprises a ferromagnetic material; and a tractive counterpart 103 comprising a cylindrical permanent magnet 104; wherein the shape, dimensions, and compositions of the backing 102, its ferromagnetic material, and permanent magnet 104 are selected such that, when applied to the skin, backing and the tractive counterpart, or combination thereof, exert a pressure on the skin of no more than 0.8 Newtons per square centimeter.

In some embodiments, the inventive device and its components can be in shapes, or have cross sections, other than a rectangle, rectangular prism, circle, or cylinder. The selection of shapes will depend, for example, on the pole of magnet(s) used.

Devices with Two Microneedle Patches

In some embodiments, the part heretofore described as a tractive counterpart is, or comprises, a second microneedle patch. Thus, by reference to FIG. 8, in some embodiments the invention comprises:
  a. a first microneedle patch 100 comprising a first plurality of drug-loaded microneedles 101 mounted on a first ferromagnetic backing 102; and
  b. a second microneedle patch 103 comprising a second plurality of drug-loaded microneedles 108 mounted on a second ferromagnetic backing 109;
  c. wherein at least one of the first and second ferromagnetic backings (102 and 109) is, or comprises, a permanent magnet.

Figure 8:
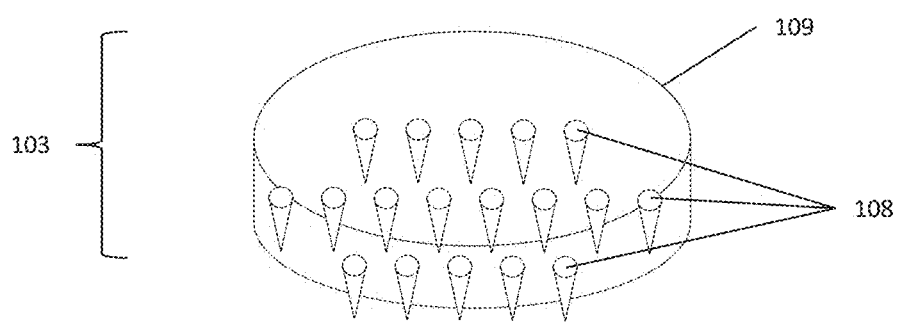
FIG. 8 is a perspective view of an embodiment of a device including a first microneedle patch and a tractive counterpart having a second microneedle patch, as described herein.
Figure 8:
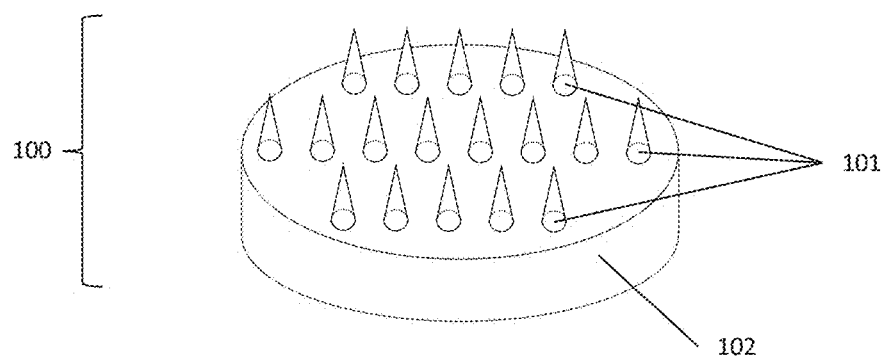

Thus, in some embodiments according to FIG. 8, each of the first and the second ferromagnetic backings (102 and 109) comprises a permanent magnet. In some other embodiments according to FIG. 8, the first ferromagnetic backing 102 comprises a permanent magnet, and the second ferromagnetic backing 109 comprises a ferromagnetic material that is not a permanent magnet. In some other embodiments according to FIG. 8, the first ferromagnetic backing 102 comprises a ferromagnetic material that is not a permanent magnet, and the second ferromagnetic backing 109 comprises a permanent magnet.

An inventive device comprising two microneedle patches provides a benefit of increasing, e.g., doubling, the surface area of skin used as an application site. Importantly, it can do so with minimal increase in the weight of the device or pressure applied to the skin, which as already stated, must be controlled so as not to inhibit capillary perfusion.

Figure 9A:
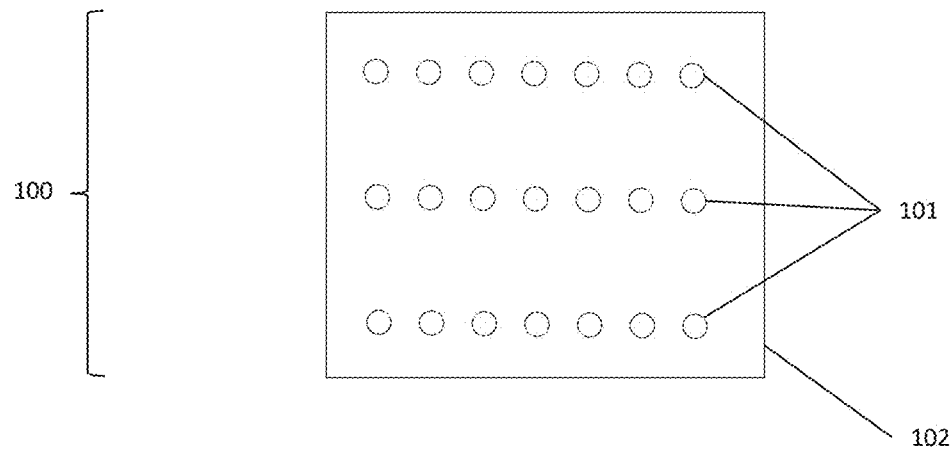
FIG. 9A is a top view of a first microneedle patch.
Figure 9B:
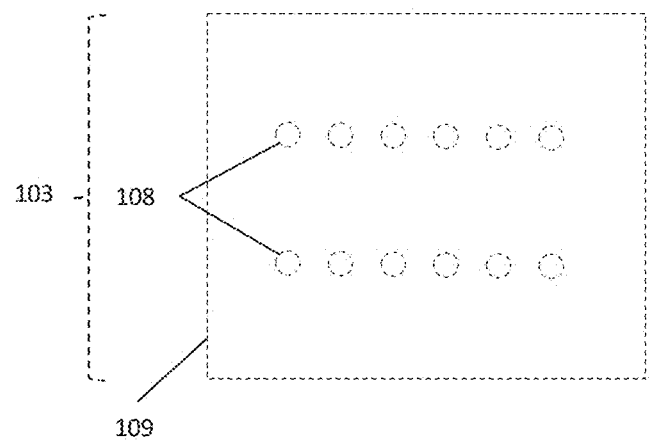
FIG. 9B is a top view of a second microneedle patch.
Figure 9C:
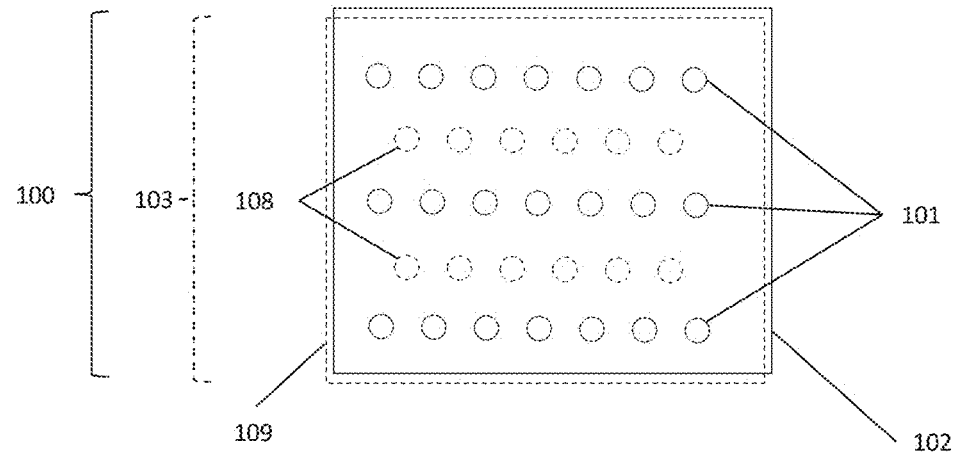
FIG. 9C is a top view of a first microneedle patch overlaid in a staggered fashion on a second microneedle patch.

In some embodiments comprising two microneedle patches, wherein each microneedle patch comprises a backing and a plurality of microneedles, further benefits (e.g., better microneedle penetration, better drug delivery, better purchase on the skin) are obtained by arranging each plurality of microneedles in a staggered fashion. The term "staggered" is defined geometrically above and can be further understood by reference to FIG. 9. FIG. 9A is a top view of a first microneedle patch 100 comprising a plurality of microneedles 101 on a substantially planar backing 102. FIG. 9B is a top view of a second microneedle patch 103 comprising a plurality of microneedles 108 on a substantially planar backing 109. The microneedles 108 are shown as dotted lines because they are located on the underside of the backing 109 and hidden from the top view. Backing 109 and the bracket numbered 103 are shown as dotted lines to differentiate them from backing 102 and solid bracket 100, respectively. The first microneedle patch 100 and second microneedle patch 103 are intended to be placed on opposite sides of the application site of a patient, e.g., the lobule of the ear, such that they overlap or substantially overlap when the first microneedle patch 100 is viewed from above. This overlap is shown in FIG. 9C, where a small amount of offset between the first microneedle patch 100 and second microneedle patch 103 is included merely for clarity of illustration. As can be seen in FIG. 9C, the first plurality of microneedles 101 is staggered with respect to the second plurality of microneedles 108. That is, there is no overlap between the two pluralities of microneedles in the dimensions shown. For purposes of staggering, various other patterns of microneedle placement can be used provided that, when the microneedle patches are overlapped as shown in FIG. 9C (consistent with their intended placement on a subject), the microneedles of the first patch are staggered with respect to the microneedles of the second patch.

Device Mass

A benefit of the present invention is that the microneedles of the microneedle patch, combined with the magnetic force that holds the microneedle patch to a tractive counterpart, can advantageously exploit shear forces to maintain purchase, i.e., keep the device in place, on the application site of the subject. In practical use, the forces that tend to counteract this purchase, e.g., to dislodge the device from application site, are gravity and natural movement of the subject. These forces are functions of the masses of the microneedle patch and the tractive counterpart. Accordingly, some preferred embodiments of the invention seek to limit the mass of the microneedle patch, the tractive counterpart, or both, while still providing the necessary tractive force, microneedle placement, and drug delivery. In this regard, a workable weight range was discovered. For example, in some embodiments, the mass of a microneedle patch or a tractive counterpart is not more than 1 $g/cm^2$ of the respective face area of the microneedle patch or tractive counterpart. In some embodiments, the mass of a microneedle patch or a tractive counterpart is not more than 1 $g/cm^2$ of the respective face area of the microneedle patch or tractive counterpart. In some embodiments, the total mass of the device is not more than 1 g/cm² of the total face areas of the microneedle patch and tractive counterpart. In some embodiments, the mass of a microneedle patch is not more than 1 g. In some embodiments, the mass of a tractive counterpart is not more than 1 g. In some embodiments, the mass of the microneedle patch is between about 10 mg and about 10 g. In some embodiments, the mass of the microneedle patch is between about 100 mg and about 1 g. In some embodiments, the mass of the tractive counterpart is between about 300 mg and about 3 g. In some embodiments, the mass of the tractive counterpart is between about 10 mg and about 10 g. In some embodiments, the mass of the tractive counterpart is between about 100 mg and about 1 g. In some embodiments, the mass of the tractive counterpart is between about 300 mg and about 3 g. In some embodiments, the ratio of the mass of the tractive counterpart to the mass of the microneedle patch is: between about 0.75 and 1.25; between about 1 and 1.5; between about 1 and 2; between about 2 and 5; or between about 3 and 10.

Methods of Use

The disclosure includes the use or application of a microneedle patch device on the skin, or otherwise in or on, a subject in need of a drug. The disclosure therefore includes methods of treating a disease in a subject in need thereof, the method including applying to the subject one of the devices described herein. Thus, in some embodiments, a microneedle patch device is placed on an area of skin of a subject in need of a drug. In some embodiments, a microneedle patch device is placed on a lobule of an ear of a subject in need of a drug. In some embodiments, a microneedle patch device is placed on an antihelix of an ear of a subject in need of a drug. In some embodiments, a microneedle patent device is placed on the interdigital web of a subject in need of a drug. In some embodiments, a microneedle patch device is placed on the skin of the nose or cheek, and a tractive counterpart can be placed, respectively, on the nasal mucosa or buccal mucosa. In some embodiments, a microneedle patch device is placed on an area of skin and a tractive counterpart is subcutaneously implanted under that area.

The disclosure therefore includes methods of treating a disease in a subject in need thereof, the method including implanting a tractive counterpart subcutaneously in the subject and applying a microneedle patch device to the skin of the subject over the tractive counterpart, wherein the microneedle patch and tractive counterpart are as described herein.

In some embodiments, a microneedle patch is placed on the skin such that the microneedles are horizontal when the subject is in an upright position.

The devices of the present invention are not limited for use on skin. Microneedles can be used to penetrate and deliver drugs across other epithelial barriers, for example, the buccal mucosa, nasal mucosa, conjunctiva (including the palpebral conjunctiva), or mucosa of the gastrointestinal tract. Thus, in some embodiments, a microneedle patch device is applied to a mucosal surface, and a tractive counterpart is applied to the skin such that an attractive magnet force operates between the microneedle patch and the tractive counterpart.

EXAMPLES

Example 1

The effect of various magnet and ferromagnetic counterpart configurations on skin pressure was determined, as a function of face area and magnet/counterpart distance. In each case, the mass of the configuration (magnet and ferromagnetic counterpart) was less than 1 g per cm² of face area. For this purpose, the magnets used were axially magnetized, standard neodymium disc magnets. The distances of 3.2, 5.1 and 6.4 mm were measured, with high-precision calipers, from different application sites on the body of a representative, normotensive human subject (e.g., interdigital web, ear lobule, and antihelix). These distance values also encompass natural anatomic variation on other subjects.

The resulting skin pressure values were compared to minimum systolic and diastolic blood pressure values of the subject to determine whether the configuration allowed perfusion during 100% of the cardiac cycle (Pass), a portion of the cardiac cycle (Partial), or none of the cardiac cycle (Fail). The results are presented in Table 1.

Thus, various magnet/counterpart configurations were found that allow local skin perfusion throughout the cardiac cycle (each marked as a "Pass"). For a human subject, these findings can be generalized by (1) measuring the pull force of a magnet/counterpart configuration; (2) measuring the face area; (3) calculating the skin pressure (i.e., pull force divided by face area); and (4) comparing that result to 0.8 N/cm², i.e. a minimum threshold for diastolic blood pressure in a normotensive human.

TABLE 1

Skin pressure for various magnet/ferromagnetic counterpart configurations.

| Magnet and counterpart | Distance (mm) | Pull force (N) | Face area (cm²) | Skin pressure (N/cm²) | Systolic BP (N/cm²) | Diastolic BP (N/cm²) | Result |
|---|---|---|---|---|---|---|---|
| D32 to D32 | 3.2 | 0.63 | 1.00 | 0.63 | 1.3 | 0.8 | Pass |
| D32 to SP | 3.2 | 0.15 | 1.00 | 0.15 | 1.3 | 0.8 | Pass |
| D42 to D42 | 3.2 | 1.34 | 1.00 | 1.34 | 1.3 | 0.8 | Fail |
| D42 to D42 | 3.2 | 1.34 | 3.00 | 0.45 | 1.3 | 0.8 | Fail |
| D42 to SP | 3.2 | 0.49 | 1.00 | 0.49 | 1.3 | 0.8 | Pass |
| D62 to D62 | 3.2 | 3.47 | 1.00 | 3.47 | 1.3 | 0.8 | Fail |
| D62 to D62 | 3.2 | 3.47 | 3.00 | 3.47 | 1.3 | 0.8 | Fail |
| D62 to SP | 3.2 | 1.73 | 1.00 | 1.73 | 1.3 | 0.8 | Fail |
| D62 to SP | 3.2 | 1.73 | 3.00 | 0.58 | 1.3 | 0.8 | Pass |
| D82 to D82 | 3.2 | 7.47 | 4.00 | 1.87 | 1.3 | 0.8 | Fail |
| D82 to D82 | 5.1 | 4.05 | 4.00 | 1.01 | 1.3 | 0.8 | Partial |
| D82 to D82 | 6.4 | 2.80 | 4.00 | 0.70 | 1.3 | 0.8 | Pass |
| D82 to SP | 3.2 | 4.45 | 4.00 | 1.11 | 1.3 | 0.8 | Partial |
| D82 to SP | 5.1 | 2.00 | 4.00 | 0.50 | 1.3 | 0.8 | Pass |
| D82 to SP | 6.4 | 1.20 | 4.00 | 0.30 | 1.3 | 0.8 | Pass |

SP = steel plate.

Example 2

The positional stability of a representative device comprising a magnet and ferromagnetic (or magnetic) counterpart is assessed in a controlled fashion with and without a microneedle patch.

The device comprising a microneedle patch consists of two parts. The first part is a disk-shaped, D32 neodymium magnet (about 4.76 mm diameter, axially magnetized) upon which is overlaid a disk-shaped microneedle patch (about 11.28 mm diameter) comprising about 64 drug-loaded microneedles on a rigid plastic backing. The microneedles are about 0.8 mm in height, as measured from apex to base. The microneedles are attached at their bases to a rigid, disc-shaped biocompatible plastic backing that is ~0.4 mm thick and about 11.28 mm in diameter. The backing is in turn attached to the D32 neodymium magnet, such that the microneedles apices are exposed. The second part of the device is a second D32 neodymium magnet (disc shaped, ~4.76 mm diameter, axially magnetized). Thus, in this example, the ferromagnetic counterpart is magnetic.

Thus, the face area of the first part of the device is about 1 cm$^2$; the face area of the second part is about 0.18 cm$^2$; the sum of those two face areas is 1.18 cm$^2$; and the total mass of the first part and the second part is less than 1.18 g, and therefore less than 1 g/cm$^2$.

The device lacking a microneedle patch is identical to the aforementioned device in dimensions, materials, and structure, except that it contains a smooth, continuous biocompatible surface instead of microneedles. Thus, the device consists of two parts. The first part is a disk-shaped, D32 neodymium magnet (about 4.76 mm diameter, axially magnetized) upon which is overlaid a smooth, disc-shaped biocompatible plastic backing that is ~1.2 mm thick and about 11.28 mm in diameter. The backing is in turn attached to the D32 neodymium magnet, such that the microneedle apices are exposed. The second part of the device is a second D32 neodymium magnet (disc shaped, ~4.76 mm diameter, axially magnetized).

A first test method is as follows. The first part of the device is placed on the lateral aspect of the lobule of the ear of a human subject such that: (1) the microneedles face and penetrate the lateral skin of the lobule; or (2) the smooth, continuous biocompatible surface faces the lateral skin of the lobule. The second part of the device is placed on the medial aspect of the lobule and oriented such that the first and second parts are attracted to one another by magnetic force, with the lobule in between them. The device thus placed on the lobule, the subject is instructed to stand erect and jump up and down. If desired, the maximal deceleration caused by the subject's landing can be measured by having the subject jump on a platform configured to measure force (e.g., a platform scale). The device is observed to test whether it remains in place during and after the subject's jumping or, for example, it shifts, separates, or falls off the lobule.

A second test method is as follows. A skin-like model comprising a sheet (e.g., 10 cm×10 cm) of thin (e.g., 3-5 mm) elastomeric material (e.g., silicone or polyurethane) is selected such that, when the device is placed on the sheet as described in the preceding paragraph, the thickness of the sheet between the first and second parts of the device is about 3 mm. The device is placed approximately in the center of the sheet. The sheet is suspended by a cord that is securely attached near one boundary of the sheet. A weight, e.g., 50 g, is securely attached near an opposite boundary of the sheet. The sheet is then lifted, e.g., 1 m above its resting height so that when it returns to its resting height and the cord is taut, the sheet, weight, and device are rapidly decelerated. If desired, the maximal deceleration can be measured by suspending the cord from an apparatus (e.g., a hanging scale) configured to measure force. The device is observed to test whether it remains in place during and after the sheet's falling or, for example, it shifts, separates, or falls off the sheet.

According to the aforementioned test methods, it is expected that the device comprising a microneedle patch will not shift, separate or fall under conditions that cause the device comprising a smooth surface to shift, separate, and/or fall. In controlled comparisons where the minimum deceleration necessary to cause each of the two devices to shift, separate, and/or fall, it is expected that the device comprising a microneedle patch will require higher deceleration, compared to the device comprising a smooth surface, to shift separate, and/or fall.

Therefore, it is expected that the inventive devices comprising a microneedle patch will provide superior purchase on the skin with pressures that do not interfere with skin perfusion, e.g., pressures on that skin that are less than 0.8 N/cm$^2$.

Example 3

A device comprising two microneedle patches, each comprising a permanent magnet, is constructed, wherein the microneedles are staggered. The first microneedle patch comprises a disk-shaped, D32 neodymium magnet (about 4.76 mm diameter, axially magnetized) upon which is overlaid a disk-shaped microneedle patch (about 11.28 mm diameter) comprising about 32 drug-loaded microneedles on a rigid plastic backing. The microneedles are about 0.8 mm in height, as measured from apex to base. The microneedles were attached at their bases to a rigid, disc-shaped biocompatible plastic backing that is ~0.4 mm thick and about 11.28 mm in diameter. The backing is in turn attached to the D32 neodymium magnet, such that the microneedles apices are exposed. The second microneedle patch, like the first microneedle patch, comprises a The first microneedle patch comprises a disk-shaped, D32 neodymium magnet (about 4.76 mm diameter, axially magnetized) upon which is overlaid a disk-shaped microneedle patch (about 11.28 mm diameter) comprising about 32 drug-loaded microneedles on a rigid plastic backing. The microneedles are likewise about 0.8 mm in height, as measured from apex to base. The microneedles were attached at their bases to a rigid, disc-shaped biocompatible plastic backing that is ~0.4 mm thick and about 11.28 mm in diameter. The backing is in turn attached to the D32 neodymium magnet, such that the microneedles apices are exposed. The first microneedle patch and the second microneedle patch are oriented such that the microneedles of the first microneedle patch are staggered with reference to the microneedles of the second microneedle patch.

Thus, the face area of the first microneedle patch is about 1 cm$^2$; the face area of the second microneedle patch is about 1 cm$^2$; the sum of those two face areas is 2 cm$^2$; and the total mass of the first part and the second part is less than 2 g, and therefore, less than 1 g/cm$^2$.

According to the aforementioned test methods, it is expected that the device comprising two microneedle patches with staggered microneedles will not shift, separate or fall under conditions that cause the device comprising a smooth surface to shift, separate, and/or fall.

Therefore, it is expected that the inventive devices comprising two microneedle patches, wherein the microneedles are staggered as described above, will provide superior purchase on the skin with pressures that do not interfere with skin perfusion, e.g., pressures on that skin that are less than 0.8 N/cm$^2$.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A device for systemic drug delivery, the device comprising:
   a first microneedle patch comprising a first plurality of drug-loaded microneedles and a first backing comprising a first permanent magnet; and
   a second microneedle patch comprising a second plurality of drug-loaded microneedles and a second backing comprising a second permanent magnet;
   wherein the first backing is substantially planar and has a face area of A1;
   wherein the second backing is substantially planar and has a face area of A2;
   wherein, when the first microneedle patch and the second microneedle patch are placed so that the first backing and the second backing are substantially parallel and no less than 3.2 mm apart at their nearest points, the attractive magnetic force between the first backing and the second backing is between 0.1 and 0.8 Newtons per square centimeter of the area that is the sum of A1 and A2.

2. The device of claim 1, wherein when the device is placed on the skin of a human, it allows capillary flow through the skin.

3. The device of claim 1, wherein the device is adapted for placement on the lobule of the human ear.

4. The device of claim 1, wherein the first plurality of drug-loaded microneedles is staggered with respect to the second plurality of drug-loaded microneedles.

5. The device of claim 1, wherein the axis of each of the first plurality of drug-loaded microneedles is substantially perpendicular to the plane of the first backing, and the axis of each of the second plurality of drug-loaded microneedles is substantially perpendicular to the plane of the second backing.

6. The device of claim 1, wherein the mass of the device is less than 1 g per square centimeter of the area that is the sum of A1 and A2.

7. The device of claim 1, wherein the mass of the first microneedle patch is less than 1 g per square centimeter of the area A1.

8. The device of claim 1, wherein the mass of the second microneedle patch is less than 1 g per square centimeter of the area A2.

9. The device of claim 1, wherein A1 is between 0.75 and 1 square centimeters, inclusive, A2 is between 0.75 and 1 square centimeters, inclusive, and the attractive magnetic force between the backings is between 0.2 and 1.6 Newtons.

* * * * *